United States Patent
Kurzmiller

(10) Patent No.: US 8,118,851 B1
(45) Date of Patent: Feb. 21, 2012

(54) SKIN MARKING METHOD

(76) Inventor: Kenneth M. Kurzmiller, Monkton, MD (US)

( * ) Notice: Subject to any disclaimer, the term of this patent is extended or adjusted under 35 U.S.C. 154(b) by 279 days.

(21) Appl. No.: 12/508,334

(22) Filed: Jul. 23, 2009

(51) Int. Cl.
*A61N 5/06* (2006.01)

(52) U.S. Cl. ............ 607/95; 607/88; 132/319; 128/898; 428/137; 428/343

(58) Field of Classification Search .................. None
See application file for complete search history.

(56) References Cited

U.S. PATENT DOCUMENTS

| | | | |
|---|---|---|---|
| 1,748,403 A | 2/1930 | Wentworth | |
| 5,052,418 A | 10/1991 | Miller | |
| 5,306,271 A | 4/1994 | Zinreich et al. | |
| 5,470,351 A | 11/1995 | Ross et al. | |
| 5,817,143 A | 10/1998 | Perry | |
| 5,836,998 A | 11/1998 | Mueller et al. | |
| D441,539 S | 5/2001 | Streit | |
| 6,264,786 B1 * | 7/2001 | Cromett | 156/289 |
| 6,365,794 B1 * | 4/2002 | Dabi et al. | 604/367 |
| 6,977,106 B2 | 12/2005 | Billings | |
| 2003/0026947 A1 | 2/2003 | Piligian | |

* cited by examiner

Primary Examiner — Sam Yao
Assistant Examiner — Lynsey Crandall

(57) ABSTRACT

A skin marking method includes positioning a panel on a person's skin. The panel has a top side, a bottom side and a peripheral edge. The panel has an artistic shape. The panel has a pressure sensitive adhesive thereon and is adhered to the skin with the adhesive. The panel is also a water resistant material. The panel and areas of the skin adjacent to the panel are exposed to light which may be natural or artificial sunlight until the areas of the skin adjacent to the panel have been tanned by the light. The panel is removed from the skin to expose an area of the skin not tanned by the light.

3 Claims, 4 Drawing Sheets

SKIN MARKING METHOD

BACKGROUND OF THE DISCLOSURE

Field of the Disclosure

The disclosure relates to selected skin area covering devices and more particularly pertains to a new selected skin area covering device for covering a selected area of skin to leave a lightened mark when adjacent areas of skin are subjected to sunlight.

SUMMARY OF THE DISCLOSURE

An embodiment of the disclosure meets the needs presented above by generally positioning a panel on a person's skin. The panel has a top side, a bottom side and a peripheral edge. The panel has an artistic shape. The panel has a pressure sensitive adhesive thereon and is adhered to the skin with the adhesive. The panel is also a water resistant material. The panel and areas of the skin adjacent to the panel are exposed to light which may be natural or artificial sunlight until the areas of the skin adjacent to the panel have been tanned by the light. The panel is removed from the skin to expose an area of the skin not tanned by the light.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
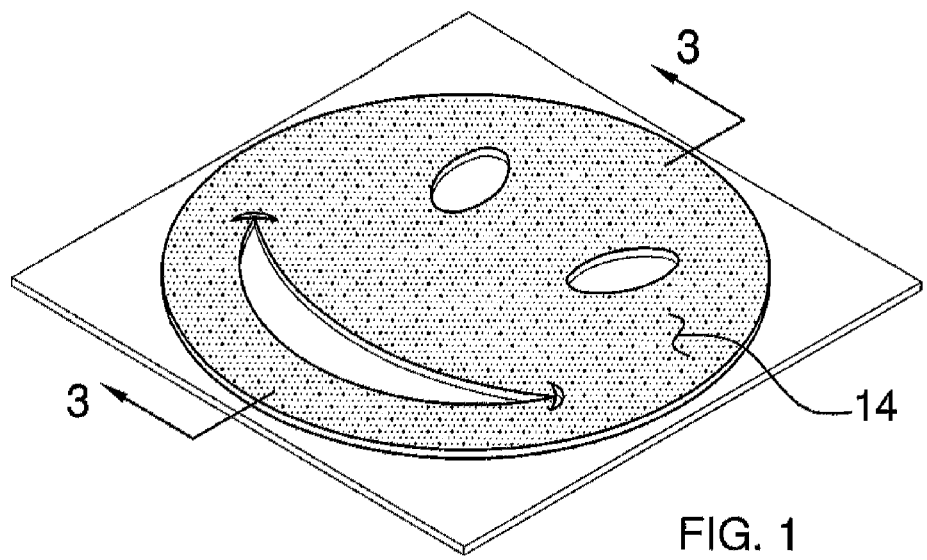
FIG. 1 is a top perspective view of a skin marking method according to an embodiment of the disclosure.

With reference now to the drawings, and in particular to FIGS. 1 through 6 thereof, a new selected skin area covering device embodying the principles and concepts of an embodiment of the disclosure and generally designated by the reference numeral 10 will be described.

Figure 2:
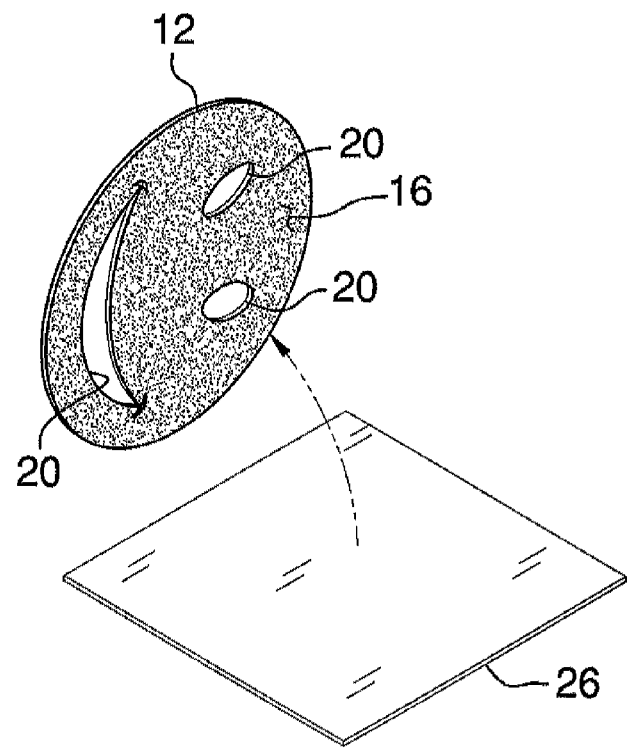
FIG. 2 is a top perspective view of an embodiment of the disclosure.
Figure 3:
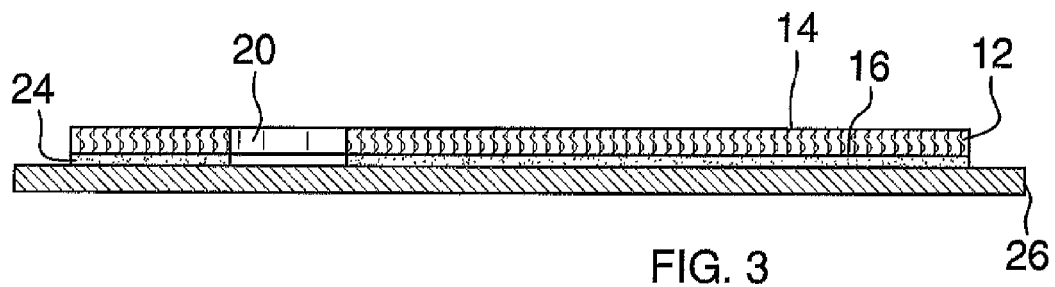
FIG. 3 is a cross-sectional view of an embodiment of the disclosure taken along line 3-3 of FIG. 1.
Figure 4:
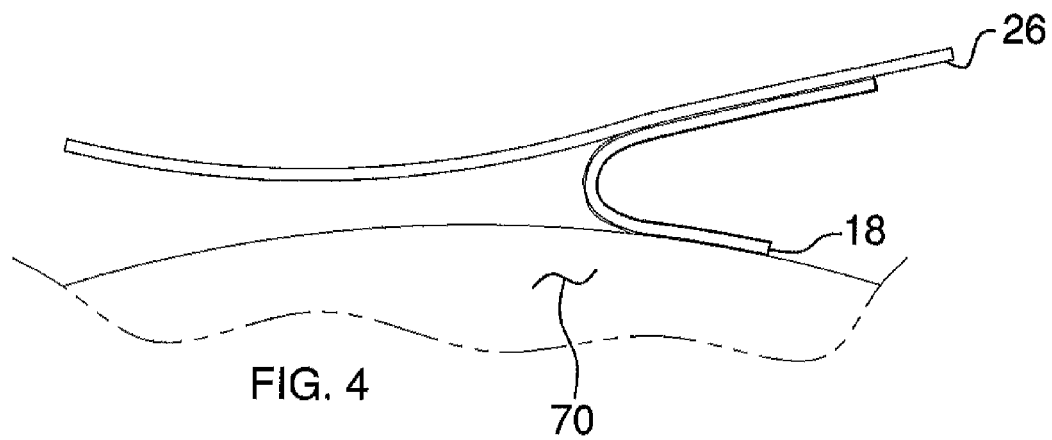
FIG. 4 is a side in-use view of an embodiment of the disclosure.
Figure 5:
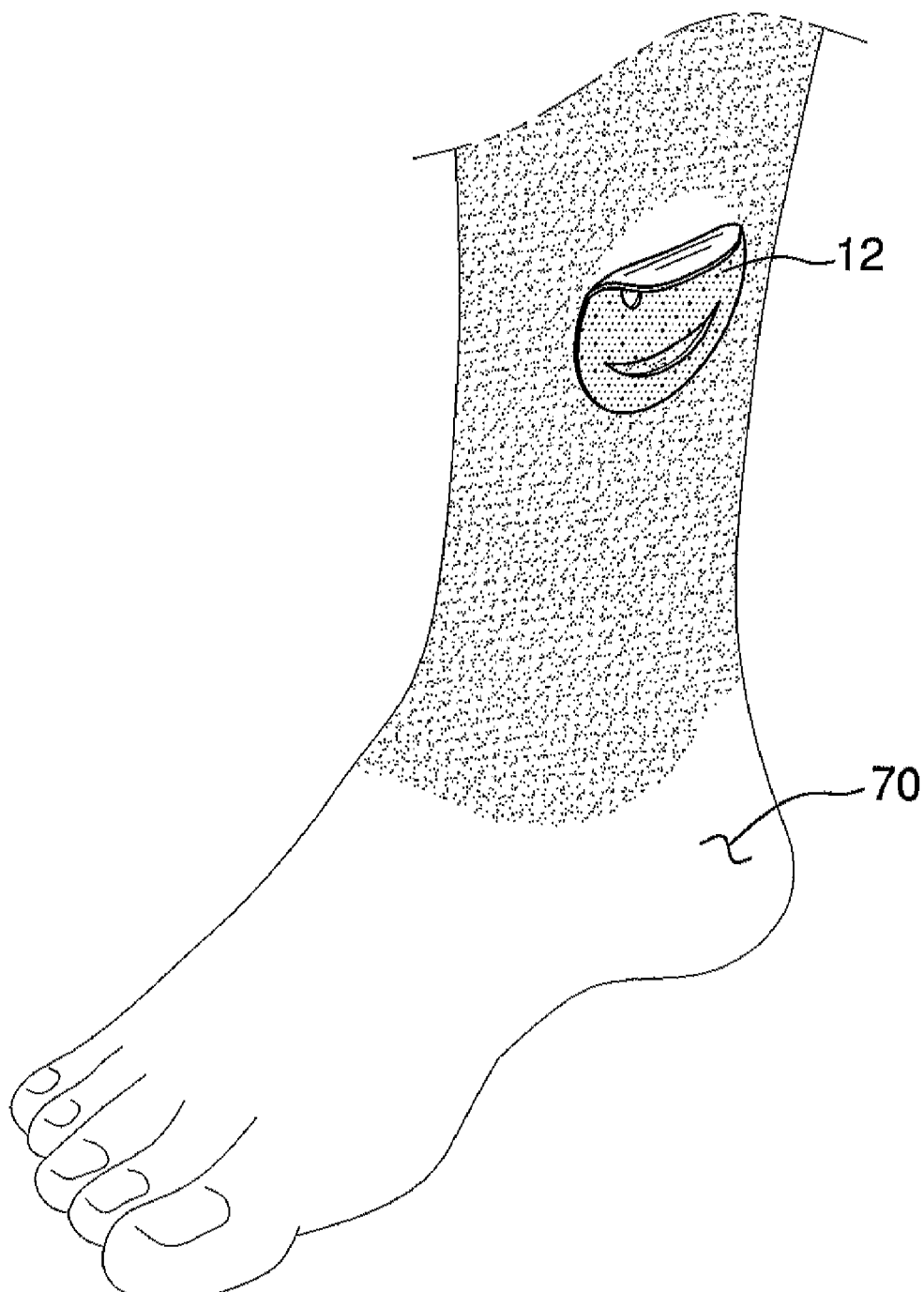
FIG. 5 is a perspective in-use view of an embodiment of the disclosure.
Figure 6:
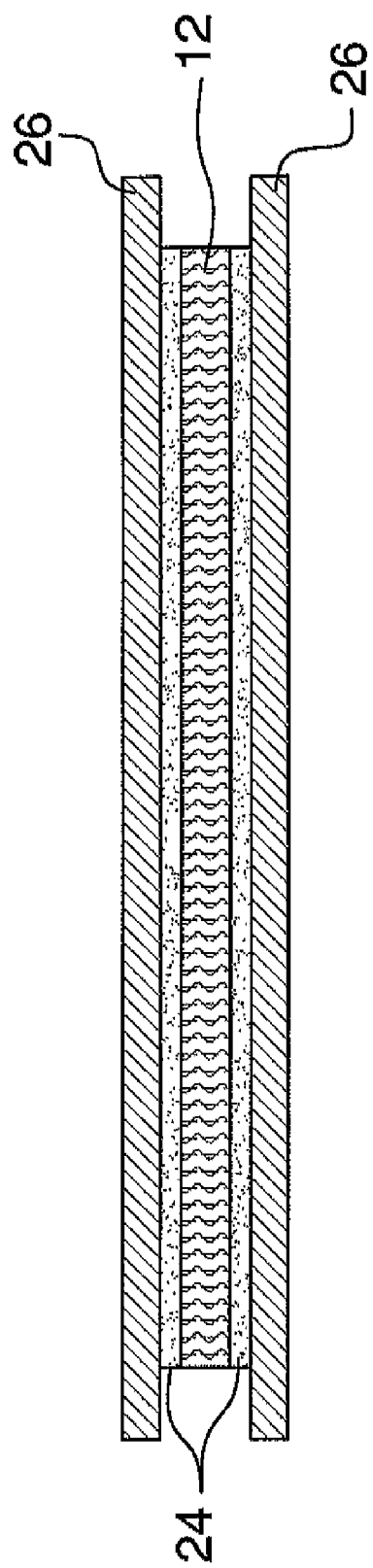
FIG. 6 is a cross-sectional view of an embodiment of the disclosure.

As best illustrated in FIGS. 1 through 6, the skin marking method 10 generally comprises positioning a flexible panel 12 on a person's skin 70. The panel 12 has a top side 14, a bottom side 16 and a peripheral edge 18. The panel 12 has an artistic shape. The shape may be any selected shape or image which may include recognizable images. Additionally, the shapes may include alphabetic or symbol indicia which may be used singularly or in tandem with other similar indicia to spell out words or phrases. In order to form the image the panel 12 may have apertures 20 extending therethrough as shown in FIG. 2. The bottom side 16 has a pressure sensitive adhesive 24 thereon which may be covered with a non-stick backing 26 to protect the adhesive 24 until it is used. The adhesive 24 allows the panel 12 to be retained on the person when the person is active, such as when the person is outside at a beach or pool. The panel 12 is adhered to the skin with the adhesive 24. As shown in FIG. 6, the adhesive 24 may perforate through the material so that it is positioned on the top 14 and bottom 16 sides so that the image may be reversed as each side will have the adhesive 24 thereon. In such an instance, the non-stick backing 26 may be positioned on both sides of the panel 12. This allows a person to selectively decide which side to adhere to the skin 70 to obtain one image, its mirror image, or both by transferring it as needed or utilizing two panels 12 having a same artistic shape with one reversed compared to the other.

The panel 12 is comprised of an air permeable material which may be a porous nylon or vinyl but which is also opaque to inhibit light transmission therethrough. The breathability of the material will ensure that the skin 70 remains healthy if the panel 12 is retained on the skin 70 for several days. Additionally, the material should be water resistant to prevent the material from dissolving or warping in water and to prevent the adhesive 24 from coming free from the panel 12.

The panel 12 and areas of the skin 70 adjacent to the panel 12 are exposed to light comprising natural or artificial sunlight until the areas of the skin adjacent to the panel 12 have been tanned by the light. What is meant by artificial light would include any type of light source, such as those found in tanning beds, which have the purpose of tanning a person's skin primarily for cosmetic reasons. However, the method 10 is primarily made for outdoor use and the panel 12 retained on the skin 70 over several days, such as at least 2 days of sun exposure.

The panel 12 is removed from the skin 70 to expose an area of the skin 70 not tanned by the light. The area which was covered by the panel 12 will have a lighter colored hue than the rest of the skin 70 to create what appears to be a reverse tattoo.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A method of leaving a mark on the skin comprising the steps of:

positioning a panel on a person's skin, said panel having a top side, a bottom side and a peripheral edge, said panel having an artistic shape, said panel having a pressure sensitive adhesive thereon, said adhesive permeating said panel and being positioned on said top and bottom sides of said panel said panel being adhered to the skin with said adhesive, said panel being comprised of a water resistant material, said panel being opaque;

exposing the panel and areas of the skin adjacent to said panel to light comprising natural or artificial sunlight until the areas of the skin adjacent to the panel have been tanned by the light; and removing the panel from the skin to expose an area of the skin not tanned by the light.

2. A method of leaving a mark on the skin comprising the steps of:

providing a panel having a top side, a bottom side and a peripheral edge, said panel having an artistic shape, said panel having a pressure sensitive adhesive thereon, said panel being opaque, said panel being adhered to the skin with said adhesive, said adhesive permeating said panel and being positioned on said top and bottom sides of said panel;

selecting a side of said panel to adhere to a person's skin and adhering said panel to the skin with said adhesive;

exposing the panel and areas of the skin adjacent to said panel to light comprising natural or artificial sunlight until the areas of the skin adjacent to the panel have been tanned by the light; and removing the panel from the skin to expose an area of the skin not tanned by the light.

3. A method of leaving a mark on the skin comprising the steps of:

positioning a panel on a person's skin, said panel having a top side, a bottom side and a peripheral edge, said panel having an artistic shape, said panel being opaque, said panel having a pressure sensitive adhesive thereon, said adhesive permeating said panel and being positioned on said top and bottom sides of said panel thereon, said panel being adhered to the skin with said adhesive, said panel being comprised of an air permeable material;

exposing the panel and areas of the skin adjacent to said panel to light comprising natural or artificial sunlight until the areas of the skin adjacent to the panel have been tanned by the light; and removing the panel from the skin to expose an area of the skin not tanned by the light.

* * * * *